United States Patent
Parthasarathy et al.

(10) Patent No.: US 6,617,136 B2
(45) Date of Patent: Sep. 9, 2003

(54) BIOLOGICAL SAMPLE PROCESSING METHODS AND COMPOSITIONS THAT INCLUDE SURFACTANTS

(75) Inventors: Ranjani V. Parthasarathy, Woodbury, MN (US); Raj Rajagopal, Woodbury, MN (US); William Bedingham, Woodbury, MN (US); Michael D. Dirksen, Stillwater, MN (US); Christopher J. Larson, Roseville, MN (US); Vinod P. Menon, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/841,272

(22) Filed: Apr. 24, 2001

(65) Prior Publication Data

US 2003/0017551 A1 Jan. 23, 2003

(51) Int. Cl.[7] .......... C12P 19/34; C12Q 1/68; C07H 19/04
(52) U.S. Cl. .......... 435/91.1; 435/6; 435/91.2; 536/26.6
(58) Field of Search .......... 435/6, 91.2; 536/26.6

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,889,818 A | 12/1989 | Gelfand et al. |

(List continued on next page.)

FOREIGN PATENT DOCUMENTS

| | | |
|---|---|---|
| EP | 624 641 B1 | 11/1994 |
| EP | 776 970 A1 | 6/1997 |
| WO | WO 89/06691 A3 | 7/1989 |
| WO | WO 89/06691 A2 | 7/1989 |
| WO | WO 92/16659 A1 | 10/1992 |
| WO | WO 96/41864 A1 | 12/1996 |
| WO | WO 99/51284 A3 | 10/1999 |
| WO | WO 99/51284 A2 | 10/1999 |
| WO | WO 99/67371 A1 | 12/1999 |

OTHER PUBLICATIONS

Roemer et al. International Genome sequencing and Analysis Conference, 2000, vol. 12, pp. 87.*
Chen et al. Nucleic Acids Research, 2001, vol. 29, No. 4, e17.*
Saiki et al., "Primer–Directed Enzymatic Amplification of DNA with a Thermostable DNA Polymerase," Science, vol. 239, pp. 487–491 (Jan. 29, 1988).
"14TH International Symposium on Microscale Separations and Analysis," California Separation Science Society, Boston Marriott Copley Place, Boston, MA; Jan. 13–18, 2001 [online] [retrieved on Apr. 3, 2001]; Retrieved from the Internet: <URL: www.casss.org/hpce2001/>, 13 pgs.
Almaraz, "Micro–Scale Capillary Electrophoresis," presented at the Mchip–based Analysis A session, 14TH International Symposium on Microscale Separations and Anaylysis, Boston Marriott Copley Place, Boston, MA, page 1 of 3, abstract, [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

(List continued on next page.)

Primary Examiner—Jezia Riley
(74) Attorney, Agent, or Firm—Christopher D. Gram; Paul W. Busse; Robert W. Sprague

(57) ABSTRACT

Compositions containing a near-IR dye and greater than about 0.5 wt-% of a surfactant selected from the group of a nonionic surfactant, a zwitterionic surfactant, and a mixture thereof, and methods for processing sample materials.

45 Claims, 4 Drawing Sheets

U.S. PATENT DOCUMENTS

| | | | |
|---|---|---|---|
| 4,951,188 | A | 8/1990 | Peter et al. |
| 4,965,188 | A | 10/1990 | Mullis et al. |
| 5,079,352 | A | 1/1992 | Gelfand et al. |
| 5,198,353 | A | 3/1993 | Hawkins et al. |
| 5,310,652 | A | 5/1994 | Gelfand et al. |
| 5,338,671 | A | 8/1994 | Scalice et al. |
| 5,352,600 | A | 10/1994 | Gelfand et al. |
| 5,374,553 | A | 12/1994 | Gelfand et al. |
| 5,405,774 | A | 4/1995 | Abramson et al. |
| 5,407,800 | A | 4/1995 | Gelfand et al. |
| 5,455,170 | A | 10/1995 | Abramson et al. |
| 5,466,591 | A | 11/1995 | Abramson et al. |
| 5,561,058 | A | 10/1996 | Gelfand et al. |
| 5,587,287 | A | 12/1996 | Scalice et al. |
| 5,618,703 | A | 4/1997 | Gelfand et al. |
| 5,618,711 | A | 4/1997 | Gelfand et al. |
| 5,641,864 | A | 6/1997 | Gelfand |
| 5,642,833 | A | 7/1997 | Ring |
| 5,674,738 | A | 10/1997 | Abramson et al. |
| 5,693,517 | A | 12/1997 | Gelfand et al. |
| 5,705,345 | A | 1/1998 | Lundin et al. |
| 5,721,123 | A | 2/1998 | Hayes et al. |
| 5,789,224 | A | 8/1998 | Gelfand et al. |
| 5,795,762 | A | 8/1998 | Abramson et al. |
| 5,858,948 | A | 1/1999 | Ghosh et al. |
| 5,861,251 | A | 1/1999 | Park et al. |
| 5,861,295 | A | 1/1999 | Goldstein et al. |
| 5,888,723 | A | 3/1999 | Sutton et al. |
| 5,919,630 | A | 7/1999 | Nadeau et al. |
| 5,939,326 | A * | 8/1999 | Chupp et al. .................. 436/43 |
| 6,015,781 | A | 1/2000 | Vinson et al. |
| 6,040,166 | A | 3/2000 | Erlich et al. |
| 6,045,727 | A | 4/2000 | Akhavan-Tafti et al. |
| 6,127,155 | A | 10/2000 | Gelfand et al. |
| 6,242,235 | B1 | 6/2001 | Shultz et al. |

OTHER PUBLICATIONS

Barta et al., "New Advances in Sample Preparation in Integrated Microfabricated Device Technology," presented at the Mchip–based Analysis A session, 14$^{TH}$ International Symposium on Microscale Separations and Analysis, Boston Marriott Copley Place, Boston, MA, page 1 of 3, abstract [online] [retrieved on Apr. 3, 2001]; Retrieved from the Internet: <URL:http://www.inmerge.com/SAPFolder/HPCE2001Results.asp?title=&author=&SessType=No+Preference&SessCode=P03&institute>; and p. 1 of 1, symposium cover sheet (Jan. 13–18, 2001) [online] [retrieved on Apr. 3, 2001]; Retrieved from the Internet: <URL: www.casss.org/hpce2001/>.

Crabtree et al., "Microchip Injection and Separation Anomalies Due to Pressure Effects," presented at the Mchip–based Analysis A session, 14$^{TH}$ International Symposium on Microscale Separations and Analysis, Boston Marriott Copley Place, Boston, MA, pp. 2–3 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Chen et al., "Plastic Microchip Electrophoresis for Genetic Screening–The Analysis of PCR Products of Fragile X(CGG)N Alleles," presented at the Mchip–based Analysis A session, 14$^{TH}$ International Symposium on Microscale Separations and Analysis, Boston Marriott Copley Place, Boston, MA, pp. 2–3 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Dunsmoor et al., "Acousto–Optical Tunable Filter for Mulicolor Detection of DNA Fragments on an Electrophoresis Microchip for Forensic Identification," presented at the Mchip–based Analysis A session, 14$^{TH}$ International Symposium on Microscale Separations and Analysis, Boston Marriott Copley Place, Boston, MA, pp. 1–2 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Giordano et al., "Infrared–Mediated Thermocycling Coupled to Microchip Electrophoresis: A Rapid DNA Amplification and Separation System," presented at the Mchip–based Analysis A session, 14$^{TH}$ International Symposium on Microscale Separations and Analysis, Boston Marriott Copley Place, Boston, MA, p. 2 of 3, abstract [online] [retrieved on Apr. 3, 2001]; Retrieved from the Internet: <URL: htttp://www.inmerge.com/SAPFolder/HPCE2001Results.asp?title=&author=SessType=No+Preference&SessCode=P03&institute>; and p. 1 of 1, symposium cover sheet (Jan. 13–18, 2001) [online] [retrieved on Apr. 3, 2001]; Retrieved from the Internet: <URL: www.casss.org/hpce2001/>.

Hibara et al., "Interface Microchip For Ultrasensitive Thermal Lens Detection of Capillary Electrophoresis," presented at the Mchip–based Analysis A session, 14$^{TH}$ International Symposium on Microscale Separations and Analysis, Boston Marriott Copley Place, Boston, MA, p. 1 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001)[online] [retrieved on Apr. 3, 2001]; Retrieved from the Internet: <URL: www.casss.org/hpce2001/>.

Jin et al., "A Simple Method for Laser–Induced Fluorescence (LIF) Detection of SDS–Protein Complexes on Microchips Without Covalent Derivatization," presented at the Mchip–based Analysis A session, 14$^{TH}$ International Symposium on Microscale Separations and Analysis, Boston Marriott Copley Place, Boston, MA, p. 2 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Jin et al., "Post–Column Reaction and Chemiluminescence Detection of Microfabricated Chips and Chip–Based Immunoassay," presented at the Mchip–based Analysis A session, 14$^{TH}$ International Symposium on Microscale Separations and Analysis, Boston Marriott Copley Place, Boston, MA, pp. 1–2 of 3, abstract [online] [retrieved on Apr. 3, 2001]; Retrieved from the Internet: <URL:http://www.inmerge.com/SAPFolder/HPCE2001Results.asp?title=&author=&SessType=No+Preference &SessCode=P03&institute>; and p. 1 of 1, symposium cover sheet (Jan. 13–18, 2001) [online] [retrieved on Apr. 3, 2001]; Retrieved from the Internet: <URL: www.casss.org/hpce2001/>.

Kim et al., "Microfabrication of polydimethylsiloxane electrospray ionization emitters," *Journal of Chromatography A*, 2001, vol. 924, pp. 137–145.

Neill et al., "On–Chip Definition of Picolitre Sample Injection Plugs for Miniaturised Liquid Chromatography," presented at the Mchip–based Analysis A session, 14$^{TH}$ International Symposium on Microscale Separations and Analysis, Boston Marriott Copley Place, Boston, MA, p. 3 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www. casss.org/hpce2001/>.

Petersen et al., "A Microfabricated Separation Chip with Integrated Waveguidelines for In–Plane Optical Detection," presented at the Mchip–based Analysis A session, 14$^{TH}$ International Symposium on Microscale Separations and Analysis, Boston Marriott Copley Place, Boston, MA, p. 1–2 of 3, abstract [online] [retrieved on Apr. 3, 2001]; Retrieved from the Internet: <URL: www. inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www. casss.org/hpce2001/>.

Sambrook, *Molecular Cloning A Laboratory Manual*, Cold Spring Harbor, New York, 1989; cover page, title page, and table of contents: 30 pgs.

Sanders et al., "Isoelectric Focusing of Proteins Using Acousto–Optical Deflection Scanning and LIF Detection," presented at the Mchip–based Analysis A session, 14$^{TH}$ International Symposium on Microscale Separations and Analysis, Boston Marriott Copley Place, Boston, MA, p. 3 of 3, abstract [online] [retrieved on Apr. 3, 2001]; Retrieved from the Internet: <URL: http://www.inmerge.com/SAPFolder/HPCE2001Results.asp?title=&author=&SessType=No+Preference&SessCode=P03&institute>; and p. 1 of 1, symposium cover sheet (Jan. 13–18, 2001) [online] [retrieved on Apr. 3, 2001]; Retrieved from the Internet: <URL: www.casss.org/hpce2001/>.

Slyadnev et al., "Ultrafast Temperature Control in a Microchannel by Laser–Induced Photothermal Effect," presented at the Mchip–based Analysis A session, 14$^{TH}$ International Symposium on Microscale Separations and Analysis, Boston Marriott Copley Place, Boston, MA, p. 3 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Strein et al., "Recent Advances with Electrochemical Detection for Microfabricated Chips," presented at the Mchip–based Analysis A session, 14$^{TH}$ International Symposium on Microscale Separations and Analysis, Boston Marriott Copley Place, Boston, MA, p. 1 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Surmeian et al., "Formation of Liquid Membrane in Flowing Micro Channel for Study on Molecular Transport," presented at the Mchip–based Analysis A session, 14$^{TH}$ International Symposium on Microscale Separations and Analysis, Boston Marriott Copley Place, Boston, MA, pp. 1–2 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Wakida et al., "High Throughput Characterization of Organic Pollutants in Waters Using CE–Chip," presented at the Mchip–based Analysis A session, 14$^{TH}$ International Symposium on Microscale Separations and Analysis, Boston Marriott Copley Place, Boston, MA, p. 2 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

Wolfe et al., "Exploring DNA Extraction in a Microminaturized Platform," presented at the Mchip–based Analysis A session, 14$^{TH}$ International Symposium on Microscale Separations and Analysis, Boston Marriott Copley Place, Boston, MA, pp. 2–3 of 3, abstract [online] [retrieved on Apr. 3, 2001]; Retrieved from the Internet: <URL: http://www.inmerge.com/SAPFolder/HPCE2001Results.asp?title=&author=&SessType=No+Preference&SessCode=P03&institute>; and p. 1 of 1, symposium cover sheet (Jan. 13–18, 2001) [online] [retrieved on Apr. 3, 2001]; Retrieved from the Internet: <URL: www.casss.org/hpce2001/>.

Zhang, "Novel Injectors for Capillary Electrophoresis on Microchips," presented at the Mchip–based Analysis A session, 14$^{TH}$ International Symposium on Microscale Separations and Analysis, Boston Marriott Copley Place, Boston, MA, p. 1 of 3, abstract [online] [retrieved on Apr. 3, 2001]; Retrieved from the Internet: <URL: www.inmerge.com/ASPFolder/HPCE2001.Results.asp>; and p. 1 of 1, symposium cover sheet (Jan. 13–18, 2001) [online] [retrieved on Apr. 3, 2001]; Retrieved from the Internet: <URL: www.casss.org/hpce2001/>.

* cited by examiner

BIOLOGICAL SAMPLE PROCESSING METHODS AND COMPOSITIONS THAT INCLUDE SURFACTANTS

BACKGROUND

Many different chemical, biochemical, and other reactions include thermal cycling. Examples of thermal processes in the area of genetic amplification include, but are not limited to, Polymerase Chain Reaction (PCR), Sanger sequencing, etc. The reactions may be enhanced or inhibited based on the temperatures of the materials involved. Although it may be possible to process samples individually and obtain accurate sample-to-sample results, individual processing can be time-consuming and expensive.

One approach to reducing the time and cost of thermally processing multiple samples is to use a device including multiple chambers in which different portions of one sample or different samples can be processed simultaneously. When multiple reactions are performed in different chambers, however, one significant problem can be accurate control of chamber-to-chamber temperature uniformity. The need for accurate temperature control may manifest itself as the need to maintain a desired temperature in each of the chambers, or it may involve a change in temperature, e.g., raising or lowering the temperature in each of the chambers to a desired setpoint. In reactions involving a change in temperature, the speed or rate at which the temperature changes in each of the chambers may also pose a problem. For example, slow temperature transitions may be problematic if unwanted side reactions occur at intermediate temperatures. Alternatively, temperature transitions that are too rapid may cause other problems. As a result, another problem that may be encountered is comparable chamber-to-chamber temperature transition rate.

Another problem that may be encountered in those reactions in which thermal cycling is required is overall speed of the entire process. For example, multiple transitions between upper and lower temperatures may be required. Alternatively, a variety of transitions (upward and/or downward) between three or more desired temperatures may be required. In some reactions, e.g., polymerase chain reaction (PCR), thermal cycling must be repeated up to thirty or more times. Typical thermal cycling devices and methods that attempt to address the problems of chamber-to-chamber temperature uniformity and comparable chamber-to-chamber temperature transition rates, however, typically suffer from a lack of overall speed—resulting in extended processing times that ultimately raise the cost of the procedures.

One or more of the above problems may be implicated in a variety of chemical, biochemical and other processes. Examples of some reactions that may require accurate chamber-to-chamber temperature control, comparable temperature transition rates, and/or rapid transitions between temperatures include, e.g., the manipulation of nucleic acid samples to assist in the deciphering of the genetic code. See, e.g., J. Sambrook and D. W. Russell, *Molecular Cloning, A Laboratory Manual 3rd edition*, Cold Spring Harbor Laboratory (2001). Nucleic acid manipulation techniques include amplification methods such as polymerase chain reaction (PCR); target polynucleotide amplification methods, such as self-sustained sequence replication (3SR); methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR).

One common example of a reaction in which all of the problems discussed above may be implicated is PCR amplification. Traditional thermal cycling equipment for conducting PCR uses polymeric microcuvettes that are individually inserted into bores in a metal block. The sample temperatures are then cycled between low and high temperatures, e.g., 55° C. and 95° C. for PCR processes. When using the traditional equipment according to the traditional methods, the high thermal mass of the thermal cycling equipment (which typically includes the metal block and a heated cover block) and the relatively low thermal conductivity of the polymeric materials used for the microcuvettes result in processes that can require two, three, or more hours to complete for a typical PCR amplification.

Another problem experienced in the preparation of finished samples (e.g., isolated or purified samples of, e.g., nucleic acid materials such as DNA, RNA, etc.) of human, animal, plant, or bacterial origin from raw sample materials (e.g., blood, tissue, etc.) is the number of thermal processing steps and other methods that must be performed to obtain the desired end product (e.g., purified nucleic acid materials). In some cases, a number of different thermal processes must be performed, in addition to filtering and other process steps, to obtain the desired finished samples.

One example is in the preparation of a finished sample (e.g., purified nucleic acid materials) from a starting sample (e.g., a raw sample such as blood, bacterial lysate, etc.). To obtain a purified sample of the desired materials in high concentrations, the starting sample must be prepared for, e.g., PCR, after which the PCR process is performed to obtain a desired PCR product. The PCR product is then subject to further manipulation such as sequencing, ligation, electrophoretic analysis, etc.

One method of improving conventional thermal cycling processes involves the use of electromagnetic radiation and energy absorbing pigments and dyes to absorb the radiation and convert it to thermal energy. The use of electromagnetic radiation absorbers such as pigments and dyes can interfere with reactions that involve the use of an enzyme. The enzyme can be deactivated, thereby preventing the formation of the desired products, e.g., PCR amplification products. Thus, there is a need for methods that allow for the use of electromagnetic radiation and absorbers such as dyes without adverse affects on the formation of the desired reaction products.

SUMMARY OF THE INVENTION

The present invention provides various compositions and methods that involve the use of an enzyme and a dye, such as a near-infrared (near-IR or NIR) dye. Such compositions and methods are preferably used for processing sample mixtures that include biological materials. Preferred methods involve the use of thermal cycling of a sample material that includes a biological material and an enzyme through the application of electromagnetic energy. A dye is used to convert the electromagnetic energy into thermal energy and a surfactant is used to inhibit (i.e., reduce, prevent, and/or reverse) interaction between the enzyme and the dye. As used herein, inhibiting interaction between the enzyme and the dye involves reducing the interaction compared to the same system when the surfactant is not present. Preferably, inhibiting interaction between the enzyme and the dye involves preventing the interaction from occurring and/or substantially completely reversing such interaction.

The present invention provides a composition that includes a near-IR dye and greater than about 0.5 wt-% of a surfactant selected from the group of a nonionic surfactant, a zwitterionic surfactant, and a mixture thereof, wherein the composition is stable in a thermal cycling process that includes cycling (preferably, at least about 10 cycles, and more preferably at least about 40 cycles) between about 50° C. and about 95° C. Preferably, the composition also includes an enzyme, which is a polymerase or a ligase.

The present invention also provides a composition that includes a near-IR dye, at least about 1 wt-% of a surfactant selected from the group of a nonionic surfactant, a zwitterionic surfactant, and a mixture thereof, a polymerase enzyme, and a triphosphate (e.g., a dNTP), wherein the composition is stable in a thermal cycling process that includes cycling (preferably, at least about 10 cycles, more preferably, at least about 40 cycles) between about 50° C. and about 95° C. Preferably, the near-IR dye is a cyanine dye or a diimminium dye.

A preferred composition of the present invention includes a near-IR dye selected from the group of a diimminium dye, a cyanine dye, and a mixture thereof, at least about 1 wt-% of a nonionic surfactant, a polymerase enzyme, and a triphosphate, wherein the composition is stable in a thermal cycling process that includes cycling (preferably, at least about 10 cycles, more preferably, at least about 40 cycles) between about 50° C. and about 95° C.

Another preferred composition of the present invention includes a near-IR dye selected from the group of a cyanine dye, a diimminium dye, and a mixture thereof; at least about 1 wt-% of a nonionic surfactant selected from the group of esters of fatty acids and polyhydric alcohols, fatty acid alkanolamides, ethoxylated fatty acids, ethoxylated aliphatic acids, ethoxylated fatty alcohols, ethoxylated aliphatic alcohols, ethoxylated sorbitol fatty acid esters, ethoxylated glycerides, ethoxylated block copolymers with EDTA, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants, polymerizable surfactants, and mixtures thereof; a polymerase enzyme; and a triphosphate; wherein the composition is stable in a thermal cycling process comprising cycling (preferably, at least about 10 cycles, more preferably, at least about 40 cycles) between about 50° C. and about 95° C.

The present invention also provides a method of stabilizing a composition that includes a near-IR dye in a thermal cycling process that includes cycling (preferably, at least about 10 cycles, more preferably, at least about 40 cycles) between about 50° C. and about 95° C. The method includes adding at least about 1 wt-% of a surfactant selected from the group of a nonionic surfactant, a zwitterionic surfactant, and a mixture thereof, to the composition. Herein, weight percentages are based on the total weight of the composition. Preferably, the composition also includes an enzyme, preferably, a polymerase enzyme. Preferably, the surfactant is a nonionic surfactant.

The present invention also provides a method of conducting a thermal process. The method includes providing a sample mixture that includes a biological material, a near-IR dye, and greater than about 0.5 wt-% of a surfactant selected from the group of a nonionic surfactant, a zwitterionic surfactant, and a mixture thereof; and directly heating the sample mixture to a second temperature higher than the first temperature; wherein the near-IR dye is stable under a thermal cycling process that includes cycling (preferably, at least about 10 cycles, more preferably, at least about 40 cycles) between about 50° C. and about 95° C. Preferably, the method further includes cooling the sample mixture and directly reheating the sample mixture in a thermal cycling process.

Yet another method is one that involves denaturing hydrogen-bonded molecules. The method includes providing a sample mixture that includes hydrogen-bonded molecules, a near-IR dye, and greater than about 0.5 wt-% of a surfactant selected from the group of a nonionic surfactant, a zwitterionic surfactant, and a mixture thereof, at a first temperature; and directly heating the sample mixture to a second temperature higher than the first temperature effective to denature the hydrogen-bonded molecules; wherein the near-IR dye is stable under a thermal cycling process that includes cycling (preferably, at least about 10 cycles, more preferably, at least about 40 cycles) between about 50° C. and about 95° C.

As used in connection with the present invention, "thermal processing" (and variations thereof) means controlling (e.g., maintaining, raising, or lowering) the temperature of sample materials to obtain desired reactions. As one form of thermal processing, "thermal cycling" (and variations thereof) means sequentially changing the temperature of sample materials between two or more temperature setpoints to obtain desired reactions. Thermal cycling may involve, e.g., cycling between lower and upper temperatures, cycling between lower, upper, and at least one intermediate temperature, etc.

As used herein, "directly" heating a sample mixture means that the sample mixture is heated from within as opposed to heated upon transfer of thermal energy from an external source (e.g., heated container).

A composition containing a dye is "stable" in a thermal cycling process (due to the presence of a surfactant) if the dye displays no more than about a 20% decrease in absorbance relative to a control, i.e., the same composition not exposed to a thermal cycling process.

These and other features and advantages of the methods and compositions of the invention are described below with respect to illustrative and preferred embodiments of the invention.

DETAILED DESCRIPTION OF PREFERRED EMBODIMENTS OF THE INVENTION

Figure 1:
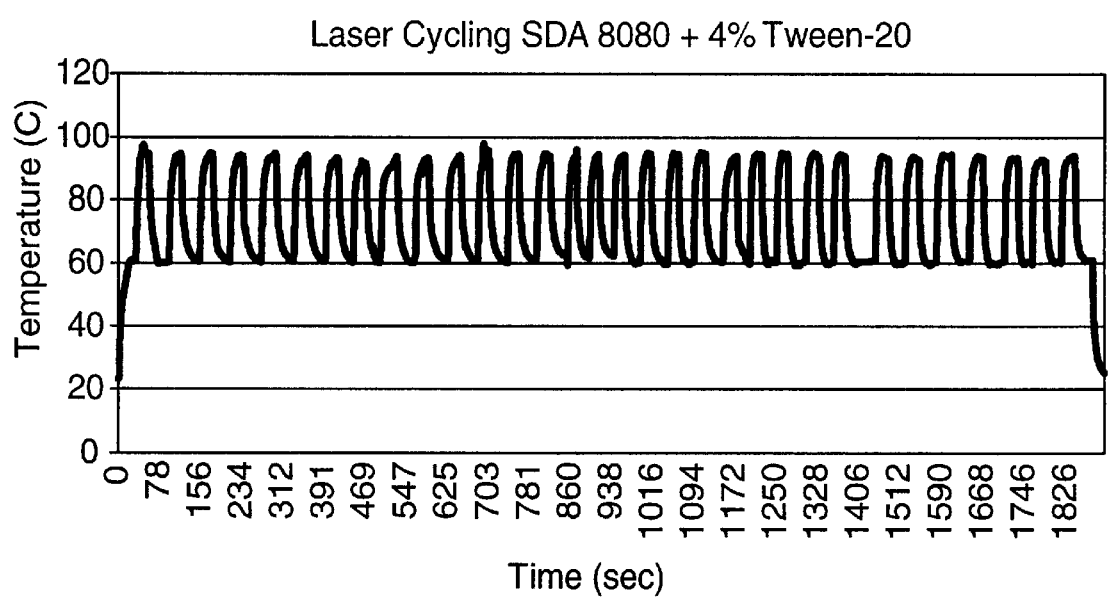
FIG. 1 is a graph of temperature versus time of a laser cycling experiment using a NIR-dye and a surfactant.

The present invention provides various compositions and methods that involve the use of a dye, such as a near-infrared (near-IR or NIR) dye, and a surfactant. Certain embodiments include the use of an enzyme in combination with a dye and a surfactant. Such compositions and methods are preferably used for processing sample mixtures (preferably, fluid samples) that include biological materials. Preferred embodiments of the present invention provide methods that involve thermal processing, e.g., sensitive chemical processes that involve the use of an enzyme such as a polymerase or a reverse transcriptase, such as PCR amplification, ligase chain reaction (LCR), self-sustaining sequence replication, enzyme kinetic studies, homogeneous ligand binding assays, and more complex biochemical or other processes that use an enzyme and require precise thermal control and/or rapid thermal variations. The methods involve the use of absorptive dyes, such as near-infrared dyes, that facilitate rapid and accurate electromagnetic energy-based or energy-derived thermal processing of sample materials.

Typically, absorptive dyes used to convert the electromagnetic energy into thermal energy are not inert in enzymatic reactions. Advantageously, a surfactant (or mixture of surfactants, preferably, a nonionic or zwitterionic surfactant, and more preferably, a nonionic surfactant, can be used to inhibit interaction between an enzyme (or mixture of enzymes) and a dye (or mixture of dyes). As used herein, inhibiting interaction between an enzyme and a dye involves reducing the interaction compared to the same system when the surfactant is not present. Preferably, inhibiting interaction between an enzyme and a dye involves preventing the interaction from occurring and/or substantially completely reversing such interaction.

Typically, absorptive dyes, particularly near-IR dyes, used to convert the electromagnetic energy into thermal energy are not stable in thermal processes (e.g., thermal cycling processes). Advantageously, a surfactant (or mixture of surfactants), preferably a nonionic or zwitterionic surfactant, and more preferably, a nonionic surfactant, can be used to stabilize a composition containing a near-IR dye in a thermal cycling process that includes cycling (preferably, at least 10 cycles, more preferably, at least 40 cycles) between about 50° C. and about 95° C. Preferably, the near-IR dye is a diimminium dye or a cyanine dye.

Typical methods of the present invention involve thermal processing of a sample mixture, such as a fluid (e.g., liquid) sample mixture, preferably one that includes a biological material. The methods generally include providing a sample mixture at a first temperature (preferably, within a range of about 0° C. to about 50° C., and more preferably, within a range of about 20° C. to about 50° C.), directly heating the sample mixture to a second temperature (preferably, within a range of about 50° C. to about 95° C.) higher than the first temperature. Preferably, the methods further include cooling the sample mixture and directly reheating the sample mixture in a thermal cycling process, which preferably includes at least about 25 cycles.

Conventional systems heat a sample mixture by heating the media surrounding the container (e.g., air, aluminum block, fluid). In contrast, the methods of the present invention provide one or more of the following advantages: noncontact heating where the fluid mixtures are heated directly without necessarily heating the surrounding container; ability to modify absorption coefficient to minimize thermal gradients, no need for support structures or heating elements (e.g., resistive heating elements, thermoelectric modules, etc.); and no need for good contact or registration with the heating block so the properties of the block (e.g., dimensions, material properties, conductivity, geometry) are not of significant importance. Also, because the "heating element" is in solution, localized heating can occur rapidly without necessarily heating the surrounding structure. In addition, because the surrounding structure is not heated, it facilitates removal of heat from the fluid compartment by diffusion. An added advantage is that one can control rate of heating by tailoring the concentration of near-IR absorber in solution (this in turn would allow one to adjust the amount of energy absorbed in the fluid compartment). In a similar fashion, the concentration of absorber can be adjusted to minimize thermal gradients occurring in the well. Because the wavelength maximum of the dye can be specified, a greater selection of light sources can be utilized (white light, uv light, near-IR laser) for noncontact heating the maximum absorption wavelength of the dye.

Recent publications have demonstrated prototype systems that use white light to heat the fluid directly, presumably using the near-IR content of light to heat water bands. In these systems, it is difficult to optimize heating (rapid, minimal thermal gradients) because of the inability to specify absorption coefficients.

Typical enzymes that can be adversely affected by large concentrations of absorptive dyes include, but are not limited to, polymerases, restriction endonucleases, and modifying enzymes (agarases, glycolysases, kinases, ligases, methylases, nucleases, proteases, phosphatases, reverse transciptases, topisomerases, and transferases). Preferably, the enzyme is a polymerase or a ligase, and more preferably, a polymerase, examples of which are well known to those of skill in the art.

Although many of the enzymes described above are adversely affected by large concentrations of absorptive dyes, some enzymes are not adversely affected. For such combinations in which the enzyme is not adversely affected by the dye, the use of a surfactant as described herein is not necessarily required to reduce, prevent, and/or reverse any adverse interaction between the dye and the enzyme; however, the surfactant may still provide advantage with respect to thermal degradation of the dye (discussed in greater detail below).

Suitable absorptive dyes that can be used to advantage in the methods of the present invention include those that will absorb energy, preferably, at a wavelength of at least about 400 nm, more preferably, at a wavelength of at least about 700 nm, and most preferably, at a wavelength of at least about 780 nm. Suitable absorptive dyes that can be used to advantage in the methods of the present invention include those that will absorb energy, preferably, at a wavelength of no greater than about 2000 nm, more preferably, at a wavelength of no greater than about 1300 nm, and most preferably, at a wavelength of no greater than about 1000 nm. These portions of the electromagnetic spectrum include the visible and near infrared (near-IR) portions. Other suitable absorptive dyes include fluorescent dyes. Preferably, the dye is a near-IR dye (e.g., a cyanine dye or a diimminium dye), an ultraviolet/visible (uv/vis) dye (e.g., dichlorophenol, indophenol, saffranin, crystal violet, and commercially available food coloring), a fluorescent dye (e.g., oligreen), or mixtures thereof. More preferably, the dye is a near-IR dye. The near-infrared (near-IR or NIR) region is typically about 700 nm to about 2000 nm, with the region of about 780 nm to about 1300 nm being of particular importance.

Classes of suitable absorptive dyes include acridine dyes, xanthene dyes, quinone-imine dyes, anthraquinone dyes, cartenoid dyes, nitro dyes, diazonium dyes, tetrazolium dyes, and di- and tri-aryl methane dyes. Classes of NIR dyes (i.e., NIR absorbers) include nitroso dyes, cyanine dyes, nigrosine dyes, triphenymethane dyes, imminium dyes, diimminium dyes, squarilium dyes, croconium dyes, nickel dithiolene dyes, quinone dyes, phthalocyanine dyes, azo dyes, indoaniline dyes, sulfur-containing dyes, vat dyes, and the like. Specific examples of suitable dyes include, but are not limited to, Methylene blue-thiazine dyes, Saffranin-Quinone imine dyes, Crystal Violet-triaryl methane dyes, Dichlorophenol indophenol-Quinone Imine dyes, as well as those listed in Table 1, etc. Preferably, the dye is a cyanine dye or a diimminium dye.

In the compositions and methods of the invention, a dye (or mixture of dyes) is used in an amount effective to heat the composition upon the application of electromagnetic energy. This amount will vary depending on the other components in the composition. Typically, such dyes can adversely affect an enzymatic reaction if used in an amount of 0.005 milligram/milliliter (mg/mL) of dye or greater. For effective heating, preferably, a dye is present in a reaction mixture at a concentration of at least about 0.1 mg/mL.

Preferably, the dyes are prepared as aqueous mixtures shortly before use. In some situations, aqueous solutions of dyes that are stored for 1 week and longer do not demonstrate benefit from the addition of a surfactant with respect to inactivation of an enzyme, although the surfactant may inhibit thermal degradation of the dye. However, when an aqueous solution of dye is added to a surfactant and stored for the same time period, it does benefit from the addition of a surfactant. Thus, for effective inhibition of inactivation of an enzyme by a dye, it is often desirable to use freshly prepared solutions.

TABLE 1

| DYE | CLASS | SOURCE |
| --- | --- | --- |
| 785 WS | Cyanine | Spectra Colors, Kearny, NJ |
| 830 WS | Cyanine | Spectra Colors, Kearny, NJ |
| IR 768 | Cyanine | Aldrich, Milwaukee, WI |
| IR 780 | Cyanine | Aldrich, Milwaukee, WI |
| IR 792 | Cyanine | Aldrich, Milwaukee, WI |
| IR 1040 | Cyanine (thiapyrilium compounds) | Aldrich, Milwaukee, WI |
| IR 1100 | Cyanine (pyrilium compounds) | Aldrich, Milwaukee, WI |
| Indocyanine green | Cyanine | Aldrich, Milwaukee, WI |
| SDA 8080 | Diimminium | H.W. Sands, Jupiter, FL |
| SDA 2141 | Cyanine | H.W. Sands, Jupiter, FL |
| SDA 8327 | Cyanine | H.W. Sands, Jupiter, FL |

Suitable surfactants that provide advantage in certain embodiments of compositions and methods of the present invention include those that will at least reduce interaction between a dye and an enzyme such that a desired product (e.g., PCR product) can be formed. Preferably, a surfactant substantially completely prevents such interaction and/or reverses such interaction. Other suitable surfactants that provide advantage in certain embodiments of compositions and methods of the present invention include those that will stabilize the dye. Preferred surfactants include nonionic and zwitterionic surfactants.

Examples of nonionic surfactants include, but are not limited to, esters of fatty acids and polyhydric alcohols, fatty acid alkanolamides, ethoxylated fatty acids, ethoxylated aliphatic acids, ethoxylated fatty alcohols, ethoxylated aliphatic alcohols, ethoxylated sorbitol fatty acid esters, ethoxylated glycerides, ethoxylated block copolymers with EDTA (ethylene diaminetetraacetic acid), ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants, and polymerizable surfactants. Examples of fluorinated surfactants include those available under the trade names FLUORAD-FS 300 (Minnesota Mining and Manufacturing Co., St. Paul, Minn.) and ZONYL (Dupont de Nemours Co., Wilmington, Del.). Examples of polymerizable (reactive) surfactants include SAM 211 (alkylene polyalkoxy sulfate surfactant available under the trade name MAZON (PPG Industries, Inc., Pittsburgh, Pa.). Examples of zwitterionic surfactants include, but are not limited to, alkylamido betaines and amine oxides thereof, alkyl betaines and amine oxides thereof, sulfo betaines, hydroxy sulfo betaines, amphoglycinates, amphopropionates, balanced amphopolycarboxyglycinates, and alkyl polyaminoglycinates. Proteins have the ability of being charged or uncharged depending on the pH; thus, at the right pH, a protein, preferably with a pI of about 8 to 9, such as modified Bovine Serum Albumin or chymotrypsinogen, could function as a zwitterionic surfactant. Specific examples include those listed in Table 2 below. Various mixtures of surfactants can be used if desired.

A surfactant is used in an amount effective to produce the desired result (e.g., inhibit inactivation of an enzyme or stabilize a dye). Preferably, a surfactant is used in an amount of at least about 0.5 wt-%, more preferably, greater than about 0.5 wt-%, even more preferably, at least about 1 wt-%, and most preferably, greater than about 1 wt-%. Preferably, no more than about 20 wt-%, and more preferably, no more than about 4 wt-% of surfactant is needed to effectively reduce the interaction between the dye and the enzyme. Such percentages are typically based on a weight per volume of a sample mixture.

TABLE 2

| SURFACTANT TRADE NAME | SURFACTANT | SUPPLIER |
| --- | --- | --- |
| NONIONIC SURFACTANTS | | |
| PLURONIC F127 | Modified oxyethylated alcohol and/or oxypropylated straight chain alcohols | Sigma St. Louis, MO |
| TWEEN 20 | Polyoxyethylene (20) sorbitan monolaurate | Sigma St. Louis, MO |
| TRITON X-100 | Octyl phenoxy polyethoxyethanol | Sigma St. Louis, MO |
| BRIJ 97 | Polyoxyethylene (10) oleyl ether | Sigma St. Louis, MO |
| NONIDET P-40 | Nonyl phenoxy poly (ethyleneoxy) ethanol | Sigma St. Louis, MO |
| TOMADOL 1-7 | Ethoxylated alcohol | Tomah Products Milton, WI |
| Vitamin E TPGS | d-Alpha tocopheryl polyethylene glycol 1000 | Eastman Kingsport, TN |
| ZWITTERIONIC SURFACTANTS | | |
| CHAPS | Cholamido propyl dimethyl ammonium propanesulfonate | Sigma St. Louis, MO |

Optionally, and preferably, radical scavengers can also be used to advantage in the compositions and methods of the present invention. Typically, continuous cycling causes a dye to be bleached (as a result of, for example, oxidization or degradation) such that it loses its color and hence, its efficiency in absorbing electromagnetic radiation. Although this could be used to advantage (as when the near-IR absorption is desirably destroyed resulting in the ability to interrogate a fluorescence signal from DNA/RNA labeled with near-IR tags), it is generally undesirable. It has been discovered that the use of a radical scavenger such as an antioxidant can inhibit this photodegradation (i.e., optical degradation) of the dye.

Suitable antioxidants include, but are not limited to, anoxomer, ascorbic acid, ascorbyl palmitate, ascorbyl stearate, butylated hydroxyanisole, butylated hydroxytoluene, t-butyl hydroquinone, calcium lactate, citric acid, clove extract, coffee bean extract, dilaurylthiodipropionate, disodium EDTA, dodecyl gallate, edetic acid, erythrobic acid, 6-ethoxy-1,2-dihydro-2,2,4-trimethylquinoline, eucalyptus extract, fumaric acid, gallic acid, gentian extract, guaiac gum, n-heptyl-p-hydroxybenzoate, heptyl paraben, hesperstin, 4-hydroxymethyl-2,6-di-t-butylphenol, isopropyl citrate, lecithin, nordihydroguairetic acid, octyl gallate, oryzanol, phosphatidyl choline, pimento extract, potassium metabisulfite, potassium sulfite, propylene glycol, rapeseed oil, rice bran extract, sage extract, sodium ascorbate, sodium sulfite, sodium tartarate, sodium thiosulfate, stannous chloride, sucrose, tocopherol, trihydroxybutyrophenene, as well as Vitamin A and derivatives thereof, Vitamin C and derivatives thereof, Vitamin E and derivatives thereof, phenols and hindered phenols, plant extracts, gallic acid and derivatives, quinines, and lecithins. Preferably, the addition of at least about 5 micrograms in a 25-microliter reaction (i.e., at least about 0.2 mg/mL) will protect the dye from bleaching.

In certain situations, the surfactant and the dye can be the same. For example, a dye molecule could be covalently attached to a hydrophilic chain like polyethylene glycol. This would yield a molecule with surfactant-like properties. Alternatively, the dye could be directly covalently attached to a surfactant molecule.

In certain situations, the surfactant and the antioxidant can be the same. For example, an antioxidant such as Viatmin E (hydrophobic) can be attached to a hydrophilic moiety such as polyethylene glycol. An example of such a compound would be Vitamine E-TPGS (tocopherol polyethylene glycol succinate).

Other agents that can be included in the compositions and methods of the present invention include a buffer, a reference dye, and other PCR reactants, which are discussed in greater detail below. Suitable buffers typically have a pH of about 4 to about 9, such as tris-HCl at a pH of between 8 and 9. Suitable reference dyes include ROX (carboxyrhodamine), TAMRA (carboxytetramethylrhodamine), FAM (carboxy fluorescien), and Texas Red, which are fluorescent dyes. Such reference dyes are typically used at lower concentrations than the dyes used for heating purposes (e.g., the NIR dyes discussed above).

Although the methods can be used in a variety of devices, a variety of illustrative embodiments of preferred devices are described in U.S. Patent Application Serial No. 60/214,508 filed on Jun. 28, 2000 and entitled THERMAL PROCESSING DEVICES AND METHODS. Other useable device constructions may be found in, e.g., U.S. patent application Ser. No. 09/710,184 filed on Nov. 10, 2000 and entitled CENTRIFUGAL FILLING OF SAMPLE PROCESSING DEVICES, as well as U.S. Provisional Patent Application Serial No. 60/214,642 filed on Jun. 28, 2000 and entitled SAMPLE PROCESSING DEVICES, SYSTEMS AND METHODS and U.S. Provisional Patent Application Serial No. 60/237,072 filed on Oct. 2, 2000 and entitled SAMPLE PROCESSING DEVICES, SYSTEMS AND METHODS.

Regardless of the specific device, a fluid sample (e.g., solution) in a process chamber can be interrogated by electromagnetic energy of selected wavelengths (if desired). Suitable electromagnetic energy is supplied by an electromagnetic energy source that directly heats the fluid (e.g., solution) in the process chamber source and is preferably remote from the device, i.e., it is not located on the device. Examples of some suitable electromagnetic energy sources may include, but are not limited to, lasers, broadband electromagnetic energy sources (e.g., white light), etc. The electromagnetic energy source may be provided continuously or intermittently based on a variety of factors, e.g., the desired temperature of the sample materials, the rate at which thermal energy is removed from each process chamber, the desired rate of temperature change, whether the process chambers include a reflective component, etc. If the electromagnetic energy source is cycled or otherwise varied, a registration system may be used to deliver a selected amount of energy to selected process chambers and an optional additional temperature control mechanism in the form of a fluid source, e.g., pressurized air or any other suitable fluid, can be directed at the surface of the device.

The advantage of using an electromagnetic energy receptive material such as an electromagnetic absorbing dye (e.g., near infrared, visible dye) is that the sample materials in the device can be heated in the absence of physical contact with the device and without directly heating the container. For example, if the electromagnetic energy receptive material is sensitive to radio-frequency (RF) radiation, the device can be rotated such that the process chambers are resident within an RF field for sufficient time to obtain the desired heating. Similar noncontact heating may be obtained with microwave radiation, etc. It will, however, be understood that the form in which the electromagnetic radiation is provided should be compatible with the sample materials and desired reactions located within the process chambers.

The methods described herein can be used in a variety of different processes requiring thermal cycling of samples contained in the process chambers of the devices. Examples of some such processes involve chemical reactions of samples, e.g., nucleic acid amplification. For example, samples may be mixed with a polynucleotide, a polymerase (such as Taq polymerase), triphosphates, a first primer hybridizable with the sample polynucleotide, and a second primer hybridizable with a sequence complementary to the polynucleotide. Some or all of the required reagents may be present in the device as manufactured, they may be loaded into the process chambers after manufacture of the device, they may be loaded in the process chambers just before introduction of the sample, or they may be mixed with sample before loading into the process chambers.

Although polynucleotide amplification by PCR is described in the most detail herein, the devices and methods of using them may be used for a variety of other systems that involve the use of dyes (and preferably, enzymes) in thermal processes, particularly those involving polynucleotide amplification reactions, ligand-binding assays, or denaturing hydrogen-bonded molecules.

Preferred reactions may be thermally cycled between alternating upper and lower temperatures, such as PCR, or they may be carried out at a single temperature, e.g., nucleic acid sequence-based amplification (NASBA). The reactions can use a variety of amplification reagents and enzymes, including DNA ligases, RNA polymerases and/or reverse transcriptases, etc. Polynucleotide amplification reactions that may be performed using the methods of the invention include, but are not limited to: a) target polynucleotide amplification methods such as self-sustained sequence replication (3SR) and strand-displacement amplification (SDA); b) methods based on amplification of a signal attached to the target polynucleotide, such as "branched chain" DNA amplification; c) methods based on amplification of probe DNA, such as ligase chain reaction (LCR) and QB replicase amplification (QBR); d) transcription-based methods, such as ligation activated transcription (LAT) and nucleic acid sequence-based amplification (NASBA); and e) various other amplification methods, such as repair chain reaction (RCR) and cycling probe reaction (CPR).

Of the potential uses for the devices and methods of the present invention, PCR is one important such use, although it should be understood that the present invention is not limited to PCR amplification. PCR allows for analysis of extremely small amounts of target nucleic acid (e.g., DNA) using an excess of two oligonucleotide primers that are capable of flanking the region of the denatured molecule to be amplified and extending the nucleic acid molecule by nucleotide addition from the primers by the action of a polymerase enzyme (such as Taq DNA polymerase) in the presence of free dNTPs (also referred to herein as deoxynucleotide triphosphates and/or deoxynucleoside triphosphates), resulting in a double replication of the starting target nucleic acid molecule. The nucleic acid molecules are again thermally treated to denature, and the process is repeated to form PCR amplification products (also referred to as PCR amplicons).

In some embodiments, DNA primers and probes are provided in the process chambers during manufacturing of specific devices. A DNA target sample could then be introduced into the process chambers to conduct PCR amplification of the DNA target. The target sample may include, e.g., target DNA, buffer, and polymerase enzyme.

After the target sample has been distributed to the process chambers (containing the pre-loaded primers and probes), the temperature of the materials in each of the process chambers can be raised to a selected base temperature (e.g., 60° C.) to begin the PCR amplification. A laser or other electromagnetic energy source can be used to raise the temperature of the sample materials in each of the process chambers to an upper target temperature at which, e.g., denaturing of the DNA occurs.

After reaching the target temperature, the sample materials are brought back down to the base temperature. This can occur by a variety of techniques. In one method of the present invention, the base temperature can be reached through convective cooling as the device rotates. That convective cooling alone, or in connection with conductive cooling using a base plate, impinging fluid jets, etc., preferably provides for rapid cooling of the sample materials, followed by rapid heating back up to the target temperature. The rapid heating and cooling is advantageous in that a desired number of thermal cycles can be completed in a relatively short period of time. Preferably, the methods described herein, whether for PCR or other techniques, a thermal cycling process preferably includes at least about 25 cycles, and preferably includes heating between a temperature of about 50° C. and about 95° C.

A preferred method involves the use of a device with a plurality of process chamber arrays such as those illustrated in U.S. Patent Application Ser. No. 60/214,642 filed on Jun. 28, 2000 and entitled SAMPLE PROCESSING DEVICE, SYSTEMS AND METHODS. Each of the process chamber arrays include a number of chambers that are preferably arranged generally radially on a device (such that centrifugal forces can move fluids sequentially from chamber to chamber). The chambers within each of the arrays are in fluid communication using channels or other conduits that may, in some embodiments, include valve structures to control the movement as desired.

Using such a device, starting sample material, e.g., lysed blood cells, is provided in a loading chamber. A filter is preferably provided to filter the starting sample material as it moves from the loading chamber to a first process chambers. The first process chambers preferably include suitable PCR primers as supplied, e.g., dried down in each of the chambers. Each of the chambers may include the same primer or different primers depending on the nature of the investigation being performed on the starting sample material. One alternative to providing the primers in the process chambers before loading the sample is to add a suitable primer to the loading chamber with the starting sample material (provided that the primer is capable of passing through the filter, if present).

After locating the starting sample material and any required primers in the process chambers, the materials in the process chambers are thermally cycled under conditions suitable for PCR amplification of the selected genetic material.

After completion of the PCR amplification process, the materials in each of the first process chambers may be moved through another filter chamber (one filter chamber for each process chamber) to remove unwanted materials from the amplified materials, e.g., PCR primers, unwanted materials in the starting sample that were not removed by filter, etc. The filter chambers may, for example, contain size exclusion substances, such as permeation gels, beads, etc. (e.g., MicroSpin or Sephadex available from Amersham Pharmacia Biotech AB, Uppsala, Sweden).

After clean-up of the sample materials in the filter chambers, the filtered PCR amplification products from each of the first process chambers are moved into a pair of multiplexed second process chambers for, e.g., Sanger sequencing of the genetic materials amplified in the first process chambers through appropriate control of the thermal conditions encountered in second process chambers.

The present invention also provides devices for thermal processing of sample materials. The sample materials may be located in a plurality of process chambers in the device which, in various aspects, may include one or more of: a reflective layer (e.g., a metallic layer); baffle structures to enhance cooling during rotation of the device; capture plugs to capture filtering materials; valve mechanisms capable of being selectively opened, thermal indicators for monitoring/controlling the temperatures in process chambers, absorptive materials in the process chambers to enhance energy absorption, etc. In various embodiments, the devices may include reagents, filters, and other sample processing materials in the process chambers.

Among the thermal control advantages of the devices of the present invention are chamber-to-chamber temperature uniformity, comparable chamber-to-chamber temperature transition rates, and the increased speed at which thermal energy can be added or removed from the process chambers. Among the device features than can contribute to these thermal control advantages are the inclusion of a reflective layer (e.g., metallic) in the device, baffle structures to assist in removing thermal energy from the device, and low thermal mass of the device. By including thermal indicators in the devices, enhanced control over chamber temperature may be achieved even as the device is rotated during processing.

Figure 2:
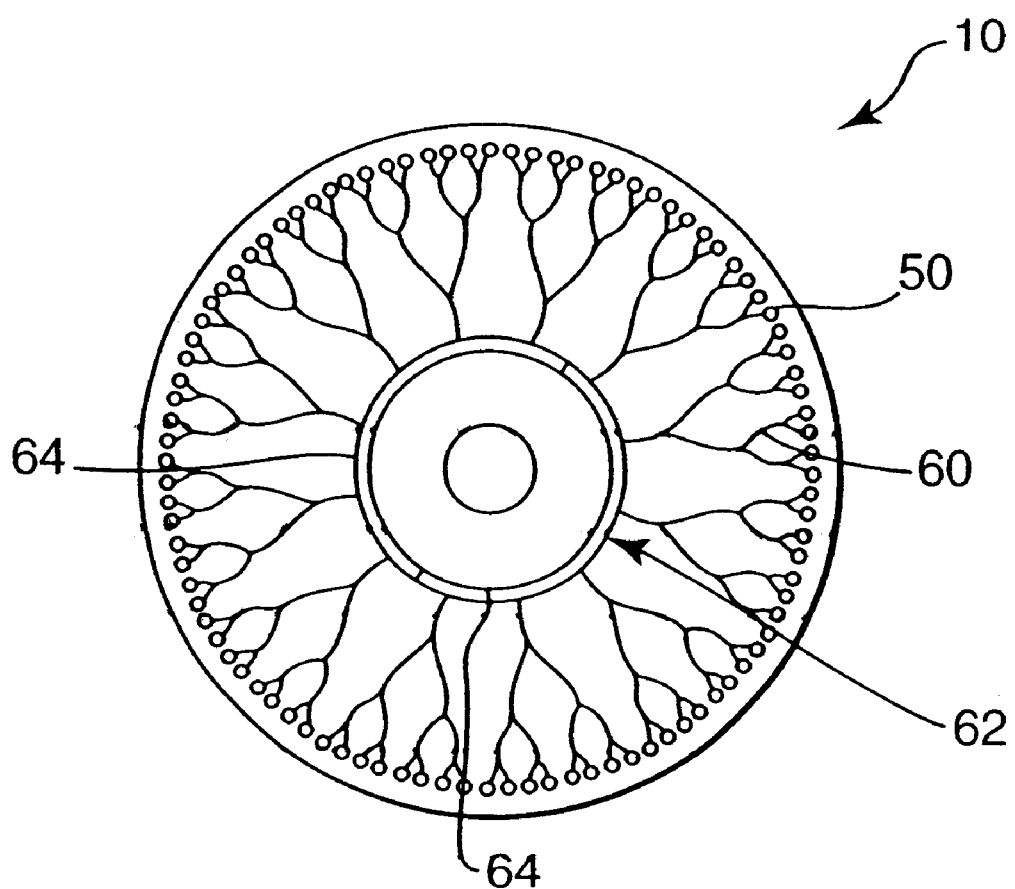
FIG. 2 is a top plan view of one device according to the present invention.

One illustrative device manufactured according to the principles of the present invention is illustrated in FIG. 2. The device 10 is preferably in the shape of a circular disc as illustrated in FIG. 1, although any other shape than can be rotated could be used in place of the preferred circular disc.

The device includes a plurality of process chambers 50, each of which defines a volume for containing a sample and any other materials that are to be thermally cycled with the sample. The illustrated device 10 includes ninety-six process chambers 50, although it will be understood that the exact number of process chambers provided in connection with a device manufactured according to the present invention may be greater than or less than ninety-six, as desired.

The process chambers 50 in the illustrative device 10 are in the form of chambers, although the process chambers in devices of the present invention may be provided in the form of capillaries, passageways, channels, grooves, or any other suitably defined volume.

The process chambers 50 are in fluid communication with distribution channels 60 that, together with loading port 62, provide a distribution system for distributing samples to the process chambers 50. Introduction of samples into the device 10 through the loading port 62 may be accomplished by rotating the device 10 about a central axis of rotation such that the sample materials are moved outwardly due to centrifugal forces generated during rotation. Before the device 10 is rotated, the sample can be introduced into the loading port 62 for delivery to the process chambers 50 through distribution channels 60. The process chambers 50 and/or distribution channels 60 may include ports through which air can escape and/or features to assist in distribution of the sample materials to the process chambers 50. Alternatively, it may be possible to provide a closed distribution system, i.e., a system in which materials may be introduced through an opening through which air within the process chambers 50 and/or distribution channels 60 also escapes during the distribution process. In another alternative, sample materials could be loaded into the process chambers 50 under the assistance of vacuum or pressure.

The illustrated device 10 includes a loading port 62 with two chambers 64 that are isolated from each other. As a result, a different sample can be introduced into each chamber 64 for loading into the process chambers 50 that are in fluid communication with the respective chamber 64 of the loading port 62 through distribution channels 60. It will be understood that the loading port 62 may contain only one chamber or that any desired number of chambers 64, i.e., two or more chambers 64, could be provided in connection with the device 10.

Figure 3:
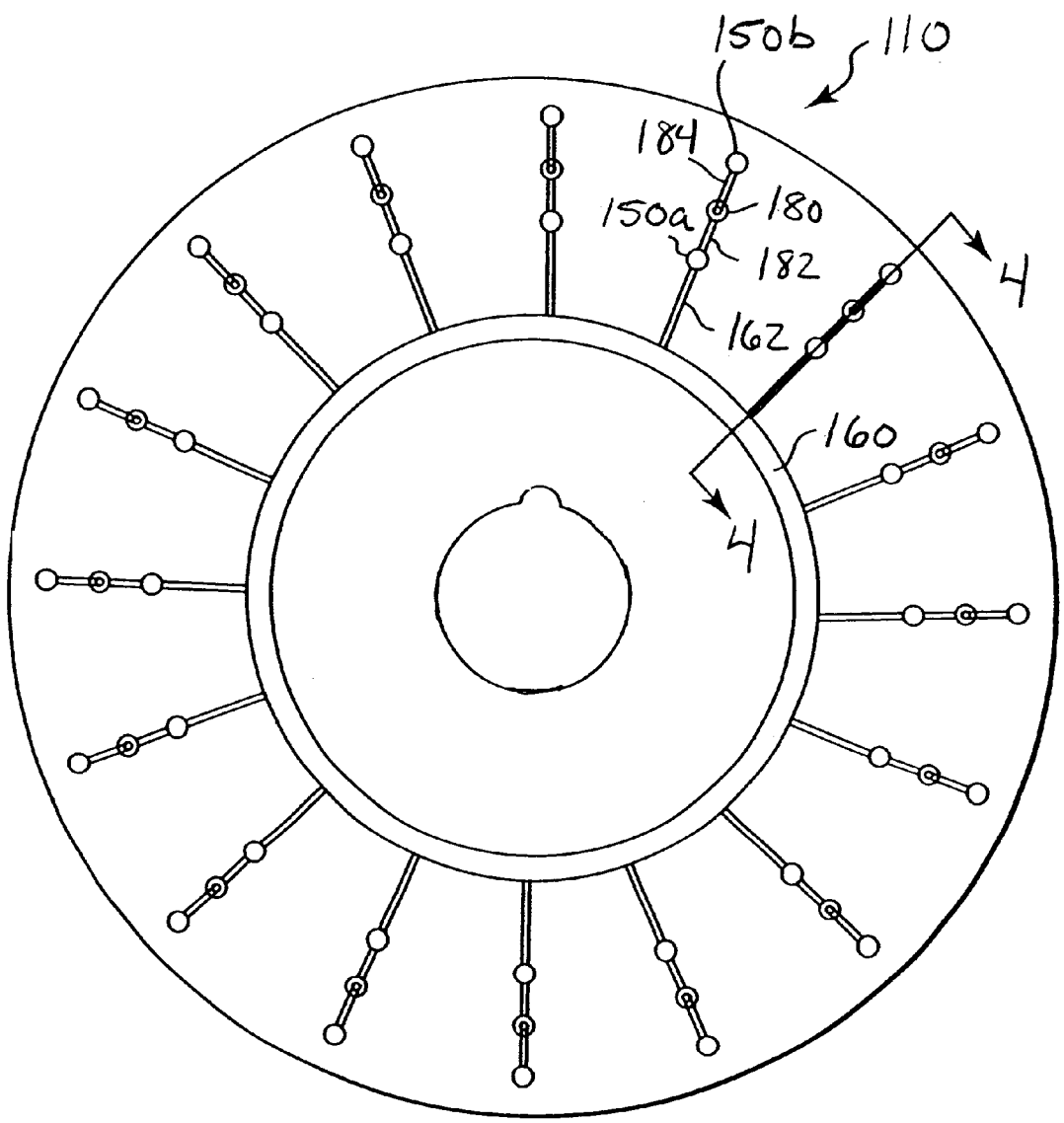
FIG. 3 is a top plan view of another device according to the present invention.
Figure 4:
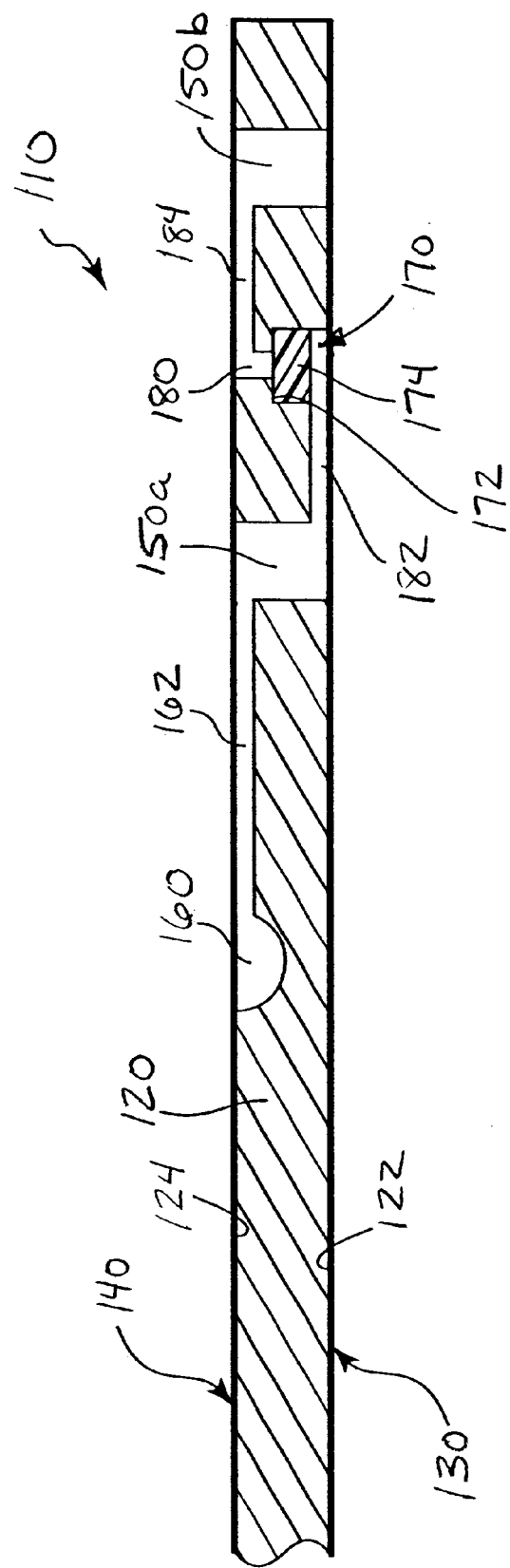
FIG. 4 is a cross-sectional view of the device of FIG. 3 taken along line 4—4 in FIG. 3.

FIGS. 3 & 4 illustrate another embodiment of a device and methods according to the present invention. The device 110 includes a number of sets of interconnected process chambers that can be described as process chamber arrays in connection with the present invention. The device 110 includes a first cover layer 130 attached to a first major side 122 of the substrate 120 and a second cover layer 140 attached to a second major side 124 of the substrate 120. The substrate 120 and cover layers 130 and 140 may be attached by any suitable technique or techniques, including, but not limited to, adhesives, welding (chemical and/or thermal), etc.

The first cover layer 130 may be homogeneous or it may include multiple sub-layers. It may be preferred that the first cover layer 130 be reflective for electromagnetic energy of selected wavelengths as described above. The second cover layer 140 may include, e.g., an adhesive on a carrier layer, both of which may be optically clear or otherwise transmissive to electromagnetic energy of selected wavelengths.

Among the features formed in the substrate 120 are a loading chamber 160 that, in the illustrated embodiment, is in the form of an annular ring. Each of the process chamber arrays also includes inner or first process chambers 150a and outer or second process chambers 150b located further out radially from a center of the device 110.

The loading chamber 160 is in fluid communication with the inner process chamber 150a through channel 162. As a result, rotation of the device 110 about its center will force sample material to move from the loading chamber 160 into the first process chamber 150a where the first thermal processing of the sample material may be performed.

The process chamber arrays also include a valve 170 located between and separating the pair of inner and outer process chambers 150a and 150b. The valve 170 is normally closed when the device 110 is supplied to a user to prevent movement of the sample material from the first process chamber 150a into the second process chamber 150b.

The valve 170 may preferably be located within a via 180 that is in fluid communication with inner process chamber 150a through channel 182 on one side and in fluid communication with the outer process chamber 150b through channel 184 on the opposite side. It may be preferred that the via 180 be formed such that it extend between the first and second major surfaces 122 and 124 of the substrate 120 as depicted.

The valve 170 includes an impermeable disc 172 that prevents fluids from moving between the process chambers 150a and 150b when it is intact. The impermeable disc 172 is preferably distinct from the substrate 120, i.e., it is preferably made of a material that is different than the material used for the substrate 120. By using different materials for the substrate 120 and the impermeable disc 172, each material can be selected for its desired characteristics.

The impermeable disc 172 may be made of any suitable material, although it may be preferred that the material of the disc 172 form voids without the production of any significant byproducts, waste, etc. that could interfere with the reactions or processes taking place in process chambers. A preferred class of materials are pigmented oriented polymeric films, such as, for example, films used to manufacture commercially available can liners or bags. A suitable film may be a black can liner, 1.18 mils thick, available from Himolene Incorporated, of Danbury, Conn. under the designation 406230E.

It may further be preferred that the impermeable disc 172 of the valve 170 include material susceptible of absorbing electromagnetic energy of selected wavelengths and converting that energy to heat, resulting in the formation of a void in the impermeable disc 172. The absorptive material may be contained within the impermeable disc 172 or coated on a surface thereof.

The valve 170 illustrated in FIG. 4 also includes an optional permeable support 174 located proximate at least one side of the impermeable disc 172. The support 174 is permeable to the fluids moving between the process chambers 150a and 150b, although it may perform some filtering functions in addition to supporting the impermeable disc 172. It may be preferred that the support 174 be somewhat resilient to assist in sealing the valve 170 by forcing the impermeable disc 172 against the surfaces in the via 180 with sufficient force to prevent fluid passage in ordinary use of the device 110.

It may be preferred that the support 174 be provided in the form of a porous disc as illustrated in FIG. 4. The porous disc support 174 may preferably be coextensive with the impermeable disc 172 used in the valve 170. Alternative forms of the support may include rings, sleeves, or any other structure or material that can support at least a portion of the impermeable disc 172 in the valve 170.

In some embodiments, it may be desirable that the porous disc support 174 reflect electromagnetic energy of selected wavelengths to assist in the opening of the valve 170 and/or prevent the electromagnetic energy from reaching any underlying fluids, sample materials, etc.

It may be preferred that the porous disc support 174 be hydrophobic to reduce or prevent fluid contact with the impermeable disc 172. Alternatively, it may be preferred that the porous disc support 174 be hydrophilic to promote fluid contact with the impermeable disc 172 of the valve 170.

Examples of suitable materials for a porous disc support may include, but are not limited to, porous plugs or membranes, including scintered polypropylene and scintered polyethylene plugs or membranes, e.g., such as those commercially available from Porex Corporation, Fairburn, Ga.

The valve 170 is opened by forming a void in the impermeable disc 172. The void may be formed by electromagnetic energy of any suitable wavelength. It may be preferred that laser energy of a suitable wavelength be used. A potential advantage of using laser energy is that the same laser used to heat the materials in the process chambers may be used to form the voids needed to place the process chambers in fluid communication with each other.

It may further be desirable to place the impermeable disc 172 of the valve 170 within a via 180 as illustrated in FIG. 4. Locating the impermeable disc 172 within a via 180 and directing electromagnetic energy of some wavelengths into the via 180 may result in some advantages in that the walls of the via 180 may reflect and/or focus at least some of the energy to assist in formation of the void in the disc 172.

EXAMPLES

Objects and advantages of this invention are further illustrated by the following examples, but the particular materials and amounts thereof recited in these examples, as well as other conditions and details, should not be construed to unduly limit this invention. All dye solutions used herein were freshly prepared (i.e., used within one day).

Example 1

Preparation of a Mixture Containing a NIR Dye and a Surfactant.

Typically, a fresh stock solution of 5 milligrams (mg) of a water-insoluble near-infrared dye (NIR dye) was dissolved in 50 microliters ($\mu$L) of dimethylsulfoxide (DMSO) and brought up in water to a final volume of 1 milliliter (mL). This was then diluted out to various concentrations of dye. The diluted dye (typically 0.2 mg/mL) was then added to a surfactant solution (typically 4 wt-%) to form a complex. The complex was added to a PCR reaction. The dyes and surfactants that were tested are listed in Tables 1 and 2, respectively.

Example 2

Formation of PCR Product in the Presence of a Surfactant.

PCR reactions were set up for a conserved sequence (327 bp) in the protease region of the genome of porcine endogenous retrovirus using a plasmid containing the PERV protease fragment, a forward primer and a reverse primer designed using a primer express program from Applied Biosystems, and AMPLITAQ DNA polymerase cocktail (commercially available from Applied Biosystems, Foster City, Calif.) and cycled in a thermocycler (9700, Applied Biosystems). The PCR reactions were typically carried out in 25-$\mu$L volumes. The NIR dye/surfactant mixture was added to the PCR cocktail to give the desired concentration of dye and surfactant in a total volume of 25 $\mu$L. A typical PCR cocktail contains 10× buffer, 2.5 $\mu$L; dNTPs, 2.0 $\mu$L (200 $\mu$M of each); forward primer, 0.5 $\mu$L (200 nM); reverse primer, 0.5 $\mu$L (200 nM); template DNA, 1.0 (1 ng/$\mu$L); Amplitaq, 0.25 $\mu$L (1.25 units); sterile water, 18.25 $\mu$L.

The products of PCR reactions were run on 1% agarose gel containing ethidium bromide and visualized using an ALPHA IMAGER (Alpha Innotech Corp., San Leandro, Calif.). In initial experiments, for example, it was found that for the dye 785 WS a final dye concentration of 0.005 mg/mL or higher inhibits PCR. However, a higher concentration of dye (0.1 mg/mL) for effective heating was needed. Thus, for all further PCR experiments, a dye concentration of 0.1 mg/mL or higher was used. The results of PCR reaction with dye/surfactant mixture showed that the dye alone inhibits PCR, while addition of surfactants restored the activity of PCR. Taq polymerase was tested from different manufacturers (Promega Corp., Madison, Wis.; Roche Biochemicals, Indianapolis, Ind.; Eppendorf, Scientific Inc., Westbury, N.Y.; Sigma, St. Louis, Mo.) and all the Taq polymerases were inhibited by 785 WS and SDA 8080. The addition of surfactants (PLURONIC or TWEEN) restored the activity of the enzyme.

Quantitative PCR using TaqMan probes or Sybr green results for SDA 8080 (0.2 mg/mL) and 785 WS (0.1 mg/mL) indicated that the dye alone inhibited the assay, while the addition of surfactants, PLURONIC F127 or TWEEN-20, restored the activity of the assay in both cases. This experiment indicated that the dye/surfactant mixture did not interfere with the fluorescence measurements of the TaqMan probes and the exonuclease activity of the Taq polymerase in addition to the polymerase activity.

In order to find out the optimum concentration of surfactant for PCR with NIR dye (785 WS and SDA 8080), the surfactant concentration in PCR reaction was varied from 0.1 wt-% to 4 wt-%. The PCR product formed was quantitated using DNA 7500 Labchip kit in Agilent 2100 Bioanalyzer (Agilent Inc, Paloalto, Calif.). The results shown in Table 3 indicate that increasing the concentration of surfactant relative to dye assists in the formation of PCR product.

TABLE 3

| | Wt % | 785 WS dye concentration (mg/mL) | PCR Product (ng/$\mu$L) | SDA 8080 dye concentration (mg/mL) | PCR Product (ng/$\mu$L) |
|---|---|---|---|---|---|
| Control | 0 | 0 | 17 | 0 | 25 |
| PLURONIC | 4 | 0 | 32* | 0 | 32* |
| F-127 | 0 | 0.1 | 0 | 0.2 | 0 |
| | 0.1 | 0.1 | 0 | 0.2 | 0 |
| | 0.5 | 0.1 | 0.1 | 0.2 | 0 |
| | 0 | 0.1 | 4.7 | 0.2 | 0 |
| | 2 | 0.1 | 12.5 | 0.2 | 0.7 |
| | 4 | 0.1 | 15 | 0.2 | 10 |

TABLE 3-continued

|  | Wt % | 785 WS dye concentration (mg/mL) | PCR Product (ng/µL) | SDA 8080 dye concentration (mg/mL) | PCR Product (ng/µL) |
|---|---|---|---|---|---|
| Control | 0 | 0 | 20.8 | 0 | 27 |
| TWEEN-20 | 4 | 0 | 28* | 0 | 28* |
|  | 0 | 0.1 | 0 | 0.2 | 0 |
|  | 0.1 | 0.1 | 0 | 0.2 | 27 |
|  | 0.5 | 0.1 | 12.7 | 0.2 | 29 |
|  | 1 | 0.1 | 19 | 0.2 | 31 |
|  | 2 | 0.1 | 23.7 | 0.2 | 22 |
|  | 4 | 0.1 | 24 | 0.2 | 19 |
| Control | 0 | 0 | 11.2 | 0 | 8.4 |
| TRITON | 4 | 0 | 23.8* | 0 | 23.8* |
| X-100 | 0 | 0.1 | 0 | 0.2 | 0 |
|  | 0.1 | 0.1 | 0 | 0.2 | 0 |
|  | 0.5 | 0.1 | 0.1 | 0.2 | 2.3 |
|  | 1 | 0.1 | 0.4 | 0.2 | 1.4 |
|  | 2 | 0.1 | 2.2 | 0.2 | 1.9 |
|  | 4 | 0.1 | 1.3 | 0.2 | 1.1 |
| Control | 0 | 0 | 27 | 0 | 28 |
| NP-40 | 4 | 0 | 24.2* | 0 | 24.2* |
|  | 0 | 0.1 | 0 | 0.2 | 0 |
|  | 0.1 | 0.1 | 0 | 0.2 | 0 |
|  | 0.5 | 0.1 | 0 | 0.2 | 23.3 |
|  | 1 | 0.1 | 0 | 0.2 | 23.7 |
|  | 2 | 0.1 | 0.3 | 0.2 | 17.2 |
|  | 4 | 0.1 | 3.8 | 0.2 | 18 |
| Control | 0 | 0 | 29 | 0 | 29 |
| BRIJ 97 | 4 | 0 | Nd | 0 | nd |
|  | 0 | 0.1 | 0 | 0.2 | 0 |
|  | 0.1 | 0.1 | 0 | 0.2 | 18.7 |
|  | 0.5 | 0.1 | 0 | 0.2 | 19.3 |
|  | 1 | 0.1 | 0 | 0.2 | 23.5 |
|  | 2 | 0.1 | 13.8 | 0.2 | 25.5 |
|  | 4 | 0.1 | 21.9 | 0.2 | 22.6 |

*denotes data obtained from a different experiment under identical PCR conditions all data averaged from experiments performed in triplicate
nd = not determined Example 3

Interaction Between an Enzyme and a Dye is Reversible Using a Surfactant.

In order to understand the reason for inhibition of PCR by a NIR dye, two separate experiments were carried out. In a first experiment (Example 3A), Taq polymerase was allowed to interact with 785 WS dye (40 micrograms (µg)) at room temperature for 25 minutes. In a second experiment (Example 3B), template DNA was allowed to interact with the same dye under the same conditions. In both experiments, the dye was removed from the enzyme or DNA template by passing the solution through a CENTRISEP column (Princeton Separations, Adelphia, N.J.). The Taq polymerase or template DNA was then used in separate reactions (25 µL) for amplifying PERV protease fragment as described in Example 2. The final dye concentration in the PCR cocktail was at 1.6 mg/mL. The results of the PCR process in Example 3A showed that Taq polymerase was inactivated by exposure to the dye thereby resulting in no amplification. From a Example 3B, the results of the PCR process showed that the dye did not have any effect on the DNA template as the removal of the dye from the template resulted in amplification of the expected fragment. From the above experiments, it was clear that the enzyme was being inhibited by the dye. In a separate experiment, Taq polymerase was allowed to react with a NIR dye (0.2 mg/mL for 785 WS and 0.3 mg/mL for SDA 8080) for 15 minutes at room temperature and the enzyme/dye mixture was added to the PCR cocktail containing different surfactants (4 wt-%). The reaction was set up to amplify PERV protease fragment as described in Example 2 and the products of the reaction were analyzed by agarose gel electrophoresis. The results of the PCR process showed that the effect of the dye on the enzyme was reversible by the addition of surfactants. The amount of the PCR product made was comparable to the controls.

Example 4

RNA Polymerase Activity is Restored by Addition of a Surfactant.

RNA polymerase reactions were set up using T7 or SP6 RNA polymerase (Epicentre Technologies, Madison, Wis.) using a linearized plasmid template containing the T7 or SP6 promoter. The reagents were used according to manufacturer's instructions. The reaction products were on 1% agarose gel and the results indicated that the NIR dye 785 WS (0.1 mg/mL) inhibited activity of both the enzymes, while addition of surfactants (PLURONIC 4 wt-%) restored the enzyme activity. The dye SDA 8080 did not inhibit the activity of both enzymes at 0.2 mg/mL.

Example 5

DNA Ligase Activity is Restored by Addition of a Surfactant.

DNA ligation reactions were set up using T4 DNA ligase (Life Technologies, Inc, Gaithesburg, Md.) using a linearized plasmid template (pET21a, Novagen, Madison, Wis.) and a DNA insert. The reagents were used according to manufacturer's instructions. *Escherichia coli* DH10B competent cells were transformed with the ligated products and transformed cells were plated on Clondisc (Clontech, Palo Alto, Calif.) with appropriate antibiotic (ampicillin at 50 µg/mL). After incubation of plates at 37° C. for 16 hours to 18 hours, the resulting colonies were counted and analysed for plasmid by miniprep and restriction digest. The NIR dyes 785 WS (0.1 mg/mL) and SDA 8080 (0.2 mg/mL) inhibited ligase activity as no colonies could be detected on the plates plated with the ligation mix containing the dye. The addition of surfactants (4 wt-% PLURONIC for 785 WS and 4 wt-% TWEEN-20 for SDA 8080) restored the activity of ligase as similar number of colonies were observed in control ligation mix (with or without surfactants) and the ligation mix containing dye/surfactant combination. In addition, all of the plasmids isolated from these plates contained the same insert as verified by restriction digest and DNA sequencing.

In addition to transformation and plating with the ligation mix, the ligated products were used as DNA template in a PCR reaction containing primers flanking the insert DNA on the plasmid template (T7 promoter and T7 terminator primers, Novagen). After PCR, the reaction products were run on 1% agarose gel and the results indicated the presence of expected DNA fragment from control ligation mix and ligation mix containing dye/surfactant combination but not from mix containing dye alone (785 WS or SDA 8080).

Example 6

A Variety of Dyes Benefit by the Addition of a Surfactant.

A variety of dyes (NIR dyes such as IR782, IR768, SDA 2141, SDA8327, IR 830 WS, fluorescent dyes like oligreen and visible dyes like dichlorophenol, indophenol, saffranin, crystal violet, and commercially available food coloring) at typical concentrations of 0.1 or 0.2 mg/mL were allowed to interact with 4 wt-% PLURONIC F127 and each mixture was added to the PCR cocktail. The reaction was set up to amplify PERV protease fragment as described in Example 2 and the products of the reaction were analyzed by agarose gel electrophoresis. The results of the PCR process showed that each of these dyes inhibited PCR, while addition of surfactants like PLURONIC F127 inhibited the effect of the dye on the reaction.

Example 7
A Surfactant Stabilizes a Dye and Assists in Preventing Thermal Degradation.

The dyes SDA 8080 and 785 WS were mixed with a variety of surfactants such as PLURONIC F-127, TWEEN-20, TRITON X-100, NP-40, BRIJ-97 and cycled in a thermocycler (9700, Applied Biosystems). Absorbance readings were taken at the beginning and end of thermal cycling using HP Chem Station (HP 8453, Agilent Technologies, Palo Alto, Calif.) at 785 nm for the 785 WS dye and 1040 nm for the SDA 8080 dye. The results indicated that the dye without the surfactant thermally degraded to levels that did not provide effective heating while the dye/surfactant mixture underwent significantly less degradation. Thus, the surfactant helps to protect thermal degradation of the dye. The data is shown in Table 4.

PCR compatible. An 813-nm diode laser source at 1.2W (1.9A) (Opto Power Corp., Tucson, Ariz.) was used to heat a 10-$\mu$L volume of near-IR dye at a concentration (0.1 mg/mL for 785 WS, 0.2 mg/mL for SDA 8080) to yield a 35° C. rise in temperature. The laser was manually turned on long enough for the temperature in a 10-$\mu$L well to increase by 35° C. (1–3 seconds) and was manually turned off when that level was attained. The temperature data was obtained using a thermocouple in the well, and the transmittance data was obtained via a power meter whose signals were digitized and graphically interpreted.

PCR thermal cycling typically requires rapid increase in temperature from 60° C. to 95° C. In a series of experiments, it was demonstrated that a 35° C. increase in temperature from 60° C. to 94° C. was obtained in under 5 seconds. This demonstrates that the thermal requirements for PCR cycling

TABLE 4

| | wt % | 785 WS (0.1 mg/mL) | | | SDA 8080 (0.2 mg/mL) | | |
|---|---|---|---|---|---|---|---|
| | | PCR Product | Thermal Degradation | Laser Stability | PCR Product | Thermal Degradation | Laser Stability |
| PLURONIC F-127 | 0 | − | 33.7% | −* | − | 92.0% | + |
| | 0.1 | − | 29.9% | Nd | − | 90.5% | nd |
| | 0.5 | + | 2.3% | Nd | − | 73.8% | nd |
| | 1 | + | 4.8% | Nd | − | 46.0% | nd |
| | 2 | + | 4.6% | Nd | + | 28.9% | nd |
| | 4 | + | 0.5% | −* | + | 22.2% | + |
| | 12 | + | nd | Nd | + | nd | nd |
| TWEEN-20 | 0 | − | 33.7% | −* | − | 92.0% | + |
| | 0.1 | + | 2.9% | Nd | + | 87.6% | nd |
| | 0.5 | + | 2.3% | Nd | + | 37.5% | nd |
| | 1 | + | 6.0% | Nd | + | 14.5% | nd |
| | 2 | + | 3.8% | Nd | + | 10.1% | nd |
| | 4 | + | 5.4% | Nd | + | 5.6% | nd |
| | 20 | + | nd | Nd | + | 4.3% | + |
| TRITON X-100 | 0 | − | 35.0% | −* | − | 95.0% | + |
| | 0.1 | − | 24.8% | Nd | − | 76.0% | nd |
| | 0.5 | + | nd | Nd | + | nd | nd |
| | 1 | + | nd | Nd | + | nd | nd |
| | 2 | + | nd | Nd | + | nd | nd |
| | 4 | + | 4.6% | Nd | + | 0.0% | nd |
| | 20 | + | nd | −* | + | 7.1% | + |
| NP-40 | 0 | − | 35.0% | Nd | − | 95.0% | + |
| | 0.1 | − | 20.2% | Nd | − | 82.1% | nd |
| | 0.5 | − | nd | Nd | + | nd | nd |
| | 1 | − | nd | Nd | + | nd | nd |
| | 2 | + | nd | Nd | + | nd | nd |
| | 4 | + | 27.4% | Nd | + | 48.8% | nd |
| Vitamin E TPGS | 0 | − | 35.0% | −* | − | 100.0% | + |
| | 0.1 | − | nd | Nd | + | nd | nd |
| | 0.5 | + | 6.5% | Nd | + | 89.5% | nd |
| | 1 | + | nd | Nd | + | nd | nd |
| | 2 | + | 4.0% | Nd | + | 88.9% | nd |
| | 4 | + | 5.3% | + | + | 92.3% | nd |
| BRIJ-97 | 0 | − | 30.0% | −* | + | 95.7% | + |
| | 0.01 | − | 79.0% | Nd | + | 86.2% | nd |
| | 0.5 | + | 95.0% | Nd | + | 67.7% | nd |
| | 1 | + | 94.5% | Nd | + | 50.0% | nd |
| | 2 | + | 94.5% | Nd | + | 29.4% | nd |
| | 4 | + | 96.0% | Nd | + | 6.0% | nd |
| | 20 | − | nd | −* | − | nd | + |

Laser stability is a measure of the absorbance drop in the dye solution upon being exposed to a laser source.
A mark of "+" means that there is less than a 20% degradation in dye absorbance over a period of 25 exposures.
A mark of "−" means that there is a greater than 20% degradation in dye absorbance over a period of 25 exposures.
*can be made laser stable after addition of antioxidant

Example 8
A NIR Dye Heats Water Efficiently with a Surfactant.

This experiment demonstrates that the dye/surfactant mixture can heat very efficiently at concentrations that are can be met at dye and surfactant concentrations that would allow DNA amplification.

In another experiment, the 10 $\mu$L well was used to see if the dye/surfactant mixture could withstand laser cycling over a period of 30 cycles. The laser power was systematically varied from 60° C. to 94° C., 30 times. FIG. 1 shows SDA 8080 being cycled repeatedly.

The laser power did not change much during the course of cycling. This indicated that the SDA 8080 dye did not bleach to any significant extent over a period of 30 cycles.

Example 9
An Antioxidant Reduces Photobleaching of a NIR Dye.

Unlike in Example 8, some dyes and dye/surfactant complexes undergo photodegradation when exposed to laser beam. Incorporation of PCR-compatible radical scavengers like ascorbic acid may significantly reduce photodegradation for some of these dyes. Addition of ascorbic acid to virtually any of the surfactants tested with 785 WS reduced photobleaching significantly. Specifically, in the case of 785 WS/BRIJ-97, the addition of ascorbic acid (typically 5 mg/mL) helped reduce the amount of photobleaching from 100% to 20% after 30 cycles. In some circumstances, rapid/controlled photodegradation may be desired. In the case of SDA 8080, addition of ascorbic acid destroyed the absorbance in the visible and near-IR region of the dye. This would allow DNA tags (fluorescent or vis/IR) to be monitored at the end of the PCR reaction.

Vitamin E-TPGS has both surfactant as well as antioxidant properties. Thus, addition of Vitamin E-TPGS (4 wt-%) to 785 WS (0.1 mg/mL) showed that the antioxidant properties became apparent as light stability was significantly increased after 30 cycles of laser exposure.

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A composition comprising a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the near-IR dye is present in an amount effective to heat the composition upon application of electromagnetic energy.

2. The composition of claim 1 wherein the near-IR dye is a diimminium dye or a cyanine dye.

3. The composition of claim 1 further comprising an enzyme.

4. A composition comprising a near-IR dye, an enzyme, and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the enzyme is a polymerase or a ligase.

5. The composition of claim 1 wherein the surfactant is a nonionic surfactant selected from the group of esters of fatty acids and polyhydric alcohols, fatty acid alkanolamides, ethoxylated fatty acids, ethoxylated aliphatic acids, ethoxylated fatty alcohols, ethoxylated aliphatic alcohols, ethoxylated sorbitol fatty acid esters, ethoxylated glycerides, ethoxylated block copolymers with EDTA, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants, polymerizable surfactants, and mixtures thereof.

6. A composition comprising a near-IR dye and greater than about 0.5 wt-% of a surfactant, wherein the composition is stable in a thermal cycling process comprising cycling between about 50° C. and about 95° C., and wherein the surfactant is a zwitterionic surfactant selected from the group of alkylamido betaines and amine oxides thereof, alkyl betaines and amine oxides thereof, sulfo betaines, hydroxy sulfo betaines, amphoglycinates, amphopropionates, balanced amphopolycarboxyglycinates, alkyl polyaminoglycinates, and mixtures thereof.

7. A composition comprising a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the dye is present at a concentration of at least about 0.005 mg/mL.

8. The composition of claim 1 wherein the surfactant is present in an amount of no greater than about 20 wt-%.

9. The composition of claim 1 further comprising a buffer.

10. A composition comprising a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the composition further comprises a triphosphate.

11. A composition comprising a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the composition further comprises a reference dye.

12. A composition comprising a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the composition further comprises an antioxidant.

13. The composition of claim 12 wherein the near-IR dye is capable of optical degradation.

14. A composition comprising a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the surfactant is an antioxidant.

15. A composition comprising:
a near-IR dye;
at least about 1 wt-% of a surfactant selected from the group of a nonionic surfactant, a zwitterionic surfactant, and a mixture thereof;
a polymerase enzyme; and
a triphosphate;
wherein the composition is stable in a thermal cycling process comprising cycling between about 50° C. and about 95° C.

16. A composition comprising a near-IR dye selected from the group of a cyanine dye, a diimminium dye, and a mixture thereof, at least about 1 wt-% of a nonionic surfactant, a polymerase enzyme, and a triphosphate, wherein the composition is stable in a thermal cycling process comprising cycling between about 50° C. and about 95° C.

17. A composition comprising:
   a near-IR dye selected from the group of a cyanine dye, a diimminium dye, and a mixture thereof;
   at least about 1 wt-% of a nonionic surfactant selected from the group of esters of fatty acids and polyhydric alcohols, fatty acid alkanolamides, ethoxylated fatty acids, ethoxylated aliphatic acids, ethoxylated fatty alcohols, ethoxylated aliphatic alcohols, ethoxylated sorbitol fatty acid esters, ethoxylated glycerides, ethoxylated block copolymers with EDTA, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, etboxylated polyoxypropylenes, polymeric silicones, fluorinated surfactants, polymerizable surfactants, and mixtures thereof;
   a polymerase enzyme; and
   a triphosphate;
   wherein the composition is stable in a thermal cycling process comprising cycling between about 50° C. and about 95° C.

18. A method of stabilizing a composition comprising a near-IR dye in a thermal cycling process comprising cycling between about 50° C. and about 95° C., the method comprising adding greater than about 0.5 wt-% of a surfactant selected from the group of a nonionic surfactant, a zwitterionic surfactant, and a mixture thereof, to the composition.

19. The method of claim 18 wherein the composition further includes an enzyme.

20. The method of claim 19 wherein the enzyme is a polymerase enzyme.

21. The method of claim 18 wherein the surfactant is a nonionic surfactant.

22. A method of conducting a thermal process, the method comprising:
   providing a sample mixture at a first temperature comprising:
      a biological material;
      a near-IR dye; and
      greater than about 0.5 wt-% of a surfactant selected from the group of a nonionic surfactant, a zwitterionic surfactant, and a mixture thereof; and
   directly heating the sample mixture to a second temperature higher than the first temperature;
   wherein the near-IR dye is stable under a thermal cycling process comprising cycling between about 50° C. and about 95° C.

23. The method of claim 22 further comprising cooling the sample mixture and directly reheating the sample mixture in a thermal cycling process.

24. A method of denaturing hydrogen-bonded molecules, the method comprising:
   providing a sample mixture at a first temperature comprising hydrogen-bonded molecules, a near-IR dye, and greater than about 0.5 wt-% of a surfactant selected from the group of a nonionic surfactant, a zwitterionic surfactant, and a mixture thereof; and
   directly heating the sample mixture to a second temperature higher than the first temperature effective to denature the hydrogen-bonded molecules;
   wherein the near-IR dye is stable under a thermal cycling process comprising cycling between about 50° C. and about 95° C.

25. A device for use in thermal processing, the device comprising:
   a plurality of process chambers in the device, each of the process chambers defining a volume for containing a sample mixture; and
   a valve located between selected pairs of the process chambers;
   wherein the sample mixture comprises a near-IR dye and greater than about 0.5 wt-% of a surfactant selected from the group of a nonionic surfactant, a zwitterionic surfactant, and a mixture thereof, and wherein the composition is stable in a thermal cycling process comprising cycling between about 50° C. and about 95° C.

26. The device of claim 25 wherein the valve comprises an impermeable disc.

27. A method of conducting a thermal cycling process comprising:
   providing a device comprising a plurality of process chambers, each of the process chambers defining a volume for containing a sample mixture;
   providing a sample mixture in at least some of the process chambers;
   delivering electromagnetic energy to the process chambers to raise the temperature of the sample mixture in the process chambers; and
   rotating the device about an axis of rotation while delivering the electromagnetic energy, wherein the temperature of the sample mixture in the process chambers is controlled as the device rotates;
   wherein the sample mixture comprises a near-IR dye and greater than about 0.5 wt-% of a surfactant selected from the group of a nonionic surfactant, a zwitterionic surfactant, and a mixture thereof, and wherein the composition is stable in a thermal cycling process comprising cycling between about 50° C. and about 95° C.

28. A method of processing sample material comprising:
   providing a device comprising a plurality of process chamber arrays, each of the process chamber arrays comprising a loading chamber, a first process chamber, and a second process chamber;
   providing a sample mixture in the loading chamber of at least one of the process chamber arrays;
   moving the sample mixture from the loading chamber into the first process chamber by rotating the device;
   controlling the temperature of the sample mixture in the first process chamber by rotating the device about an axis of rotation while delivering electromagnetic energy to the first process chamber;
   moving the sample mixture from the first process chamber to the second process chamber by rotating the device; and
   controlling the temperature of the sample mixture in the second process chamber by rotating the device about an axis of rotation while delivering electromagnetic energy to the second process chamber;
   wherein the sample mixture comprises a near-IR dye and greater than about 0.5 wt-% of a surfactant selected from the group of a nonionic surfactant, a zwitterionic surfactant, and a mixture thereof, wherein the composition is stable in a thermal cycling process comprising cycling between about 50° C. and about 95° C.

29. The method of claim 28, wherein the process chamber arrays comprise a valve located between the first process chamber and the second process chamber, and wherein the method further comprises opening the valve to move the sample mixture from the first process chamber to the second process chamber.

30. The composition of claim 10 wherein the triphosphate is a dNTP.

31. A composition comprising a near-IR dye and greater than about 05 wt-% of a surfactant selected from the group of a nonionic surfactant, a zwitterionic surfactant, and a mixture thereof, wherein the composition is stable in a thermal cycling process comprising cycling between about 50° C. and about 95° C., and wherein the near-IR dye and the surfactant form a complex.

32. The method of claim 22 wherein the thermal process comprises a thermal cycling process.

33. The method of claim 22 wherein the second temperature is greater than about 50° C.

34. The method of claim 22 wherein the biological material comprises a polymerase enzyme and a triphosphate.

35. The method of claim 22 wherein the near-IR dye is present in an amount effective to heat the composition upon application of electromagnetic energy.

36. The method of claim 22 wherein directly heating the sample mixture comprises delivering electromagnetic energy to the mixture.

37. The method of claim 24 wherein the hydrogen-bonded molecules comprise nucleic acids.

38. The method of claim 24 wherein the second temperature is greater than about 50° C.

39. The method of claim 24 wherein the sample mixture further comprises a polymerase enzyme and a triphosphate.

40. The method of claim 24 wherein the near-IR dye is present in an amount effective to heat the composition upon application of electromagnetic energy.

41. The method of claim 24 wherein directly heating the sample mixture comprises delivering electromagnetic energy to the mixture.

42. The device of claim 25 wherein the thermal processing comprises a thermal cycling process.

43. The device of claim 25 wherein the process chambers comprise one or more of: a reflective layer, a baffle structure, a capture plug, a thermal indicator, an absorptive material, and combinations thereof.

44. The device of claim 25 wherein the sample mixture further comprises a polymerase enzyme and a triphosphate.

45. The device of claim 25 wherein the new-IR dye is present in an amount effective to heat the composition upon application of electromagnetic energy.

* * * * *

UNITED STATES PATENT AND TRADEMARK OFFICE
CERTIFICATE OF CORRECTION

| | | |
|---|---|---|
| PATENT NO. | : 6,617,136 B2 | |
| APPLICATION NO. | : 09/841272 | |
| DATED | : September 9, 2003 | |
| INVENTOR(S) | : Ranjani V. Parthasarathy et al. | |

It is certified that error appears in the above-identified patent and that said Letters Patent is hereby corrected as shown below:

Column 23, line 19, delete "etboxylated" and insert -- ethoxylated --, therefor.

Column 26, line 22, delete "new" and insert -- near --, therefor.

Signed and Sealed this

Twenty-ninth Day of January, 2008

JON W. DUDAS
*Director of the United States Patent and Trademark Office*